United States Patent [19]

Jolly et al.

[11] Patent Number: 5,250,429
[45] Date of Patent: Oct. 5, 1993

[54] GLASSIFIED RESTRICTION ENZYMES

[75] Inventors: James F. Jolly, Glendale, Wis.; Jack G. Chirikjian, Potomac, Md.; Caecilia J. Huang, New Berlin, Wis.

[73] Assignee: Pharmacia P-L Biochemicals Inc., Milwaukee, Wis.

[21] Appl. No.: 763,034

[22] Filed: Sep. 20, 1991

[51] Int. Cl.$^5$ .................. C12N 9/14; C12N 9/16; C12Q 1/34; C12Q 1/44
[52] U.S. Cl. ...................... 435/196; 435/18; 435/19; 435/178; 435/183; 435/187; 435/188; 435/195
[58] Field of Search .................. 435/18, 19, 178, 183, 435/187, 188, 195, 196; 424/440

[56] References Cited

U.S. PATENT DOCUMENTS 3,300,474  1/1967  Flodin et al.
5,098,893  3/1992  Franks et al. .................. 514/54

FOREIGN PATENT DOCUMENTS 298669   12/1990  European Pat. Off.
8700196   1/1987  World Int. Prop. O.

OTHER PUBLICATIONS 10 pages Pharmacia article entitled "Ficoll for cell research", undated admitted prior art.
Pp. 5.3-5.32 of J. Sambrook et al., A Laboratory Manual, (1989).
J. George et al., 79 P.N.A.S. USA 2432-36 (1982).
W. Malyguine et al., 8 Gene 163-177 (1980).

*Primary Examiner*—Robert A. Wax
*Assistant Examiner*—Hyosuk Kim
*Attorney, Agent, or Firm*—Quarles & Brady

[57] ABSTRACT

A room temperature stable restriction enzyme in a glassified carbohydrate stabilizer is disclosed. A restriction enzyme reaction buffer containing $Mg^{+2}$ is dispersed in the stabilizer. One cleaves DNA merely by adding water and DNA to the composition. The composition can reduce glycerol-caused star activity by avoiding the need for glycerol. The composition also reduces star activity caused by high concentrations of enzymes. Another method is provided of comparing cleaved DNA samples in connection with forensic and paternity testing applications.

7 Claims, 1 Drawing Sheet

398n
R=SUCROSE

GLASSIFIED RESTRICTION ENZYMES

FIELD OF THE INVENTION

The present invention relates to improved techniques for the storage of restriction enzymes. In particular, it relates to the stable storage of restriction enzymes with reaction buffers in a glassified state.

BACKGROUND OF THE INVENTION

There are two main types of restriction endonucleases ("restriction enzymes"), type I and type II. Both types cleave double-stranded DNA molecules. Type I restriction enzymes recognize a specific DNA sequence, but cleave the DNA molecule at varied sites removed from that sequence. In contrast, type II restriction enzymes recognize a specific DNA sequence and cleave DNA molecules at or adjacent specific sequences (a "restriction site"). Type II restriction enzymes are therefore particularly useful in biological techniques such as molecular cloning, genetic mapping and DNA sequence analysis. See generally Molecular Cloning: A Laboratory Manual, J. Sambrook et al. (2nd Ed. 1989).

However, type II restriction enzymes may be quite unstable, especially in the presence of $Mg^{+2}$, which is a cofactor for some proteases. If activated, proteases can degrade a restriction enzyme. $Mg^{+2}$ is also a nutrient source for some bacteria that can contaminate and inactivate an enzyme preparation. Also, conformational and other changes to restriction enzymes can occur during improper storage. Thus, methods have been developed to reduce storage problems associated with restriction enzymes.

One well known prior art method of storage is freeze-drying. In this method, an aqueous solution of the enzyme in a conventional storage buffer and in the presence of a cryoprotectant is first frozen, typically to $-40°$ to $-50°$. Water is then removed from the biological solution and the residual material becomes more concentrated until the material crystallizes. Ice is then removed by sublimation under vacuum. When the last traces of residual moisture are removed, a dry crystalline powder remains. An active enzyme may be reconstituted from this powder.

Unfortunately, exposure of a freeze-dried product to ambient temperatures can result in significant enzyme activity loss. Additionally, restriction enzymes are often not completely freeze-stable. Further, the freeze-drying cycle may take several days and the activity of the reconstituted enzyme may not be very reproducible.

The "freeze/thaw" storage method involves mixing the enzyme with a cryoprotectant, freezing and storing, usually below $-50°$ C. and sometimes in liquid nitrogen. The enzyme is then thawed immediately before use. Some enzymes will not survive a freezing and thawing cycle. Further, this technique can be expensive (especially with respect to transportation to customers).

Another technique (the one currently in commercial widespread use) involves storing an enzyme solution at $-20°$ C. This type of refrigerated storage for restriction enzymes usually involves the addition of the cryoprotection additive glycerol to depress the freezing point and avoid freezing the enzyme. Restriction enzymes are usually stored in 50% glycerol.

A significant problem with this type of storage of restriction enzymes is that the presence of glycerol in a restriction enzyme reaction can lead to what is known as specificity relaxation (such as "star activity"). In this regard, when restriction enzyme digestions are done in the presence of glycerol, the specificity of the enzyme for a particular restriction site becomes relaxed and DNA is no longer cleaved only at that restriction site. The lack of enzyme specificity may lead to confusion as to which DNA fragments are the result of true restriction enzyme cleavage. It is generally understood that a glycerol concentration of greater than 5% can create a significant possibility of star activity in an enzymatic digest. High enzyme concentration in the DNA cleavage reaction is also known to contribute to star activity, even in the absence of glycerol. To date, the art has often sought to minimize specificity relaxation by using lower than desired concentrations of enzyme and/or longer than desired incubation times.

Another method of storing restriction enzymes involves forming a "glass" with the restriction enzyme embedded within it. A stabilizer (usually a carbohydrate) is used that is capable of forming a glass and does not interfere with DNA cleavage reactions. In the glass, the restriction enzyme is virtually immobilized and stable, even at room temperature. However, when this storage technique was used, water and appropriate salts and reagents had to be added to the glassified enzyme to create a solution capable of cleaving DNA.

The prior glassification method is therefore limited in that it required the lab worker to add the various reagents (especially $Mg^{+2}$) to activate the restriction enzyme after storage. Also, high enzyme concentrations in the cleavage reaction still would lead to star activity, even in the absence of glycerol.

A need therefore existed for an improved system of storing restriction enzymes so that the enzymes would remain stable during long-term storage at room temperature, could be activated upon reconstitution with only water and substrate DNA (without the need to separately add other chemicals), and so that star activity could be reduced even for high enzyme concentrations.

SUMMARY OF THE INVENTION

The present invention provides a glassified composition made up of a glassified carbohydrate having dispersed in it a type II restriction enzyme and $Mg^{+2}$. Preferably, the stabilizer is a carbohydrate (such as Ficoll®), and the composition also has in it all other reaction reagents needed for the composition to cleave (in the presence of additional water) DNA having a restriction site that the enzyme is capable of cleaving. The stabilizer is most preferably at least 30% of the weight of the composition, and preferably less than 1% (e.g. 0%) of the composition is glycerol.

In another aspect, a method of cleaving DNA is provided. One adds water and the DNA to the composition, and allows cleavage to occur. A high ratio of stabilizer to enzyme is preferred.

Yet another aspect the invention provides a method of comparing two DNA samples. One separately adds the samples and water to two different containers, adds the above composition to each container, allows cleavage of each DNA sample to occur, and compares the cleaved DNA samples from each container. An especially preferred enzyme is Hae III, and this method is preferably used as part of forensic or paternity tests that rely on accurate DNA digestions.

It is an object of the present invention to create a restriction enzyme storage system that permits stable room temperature storage.

It is another object of the present invention to create a method for cleaving DNA that reduces star activity even when a cleavage reaction contains high levels of enzyme.

It is yet another object to create a method that accurately compares DNA samples that have been digested with restriction enzymes.

It is another object to provide a stored restriction enzyme that can be activated by simply adding the DNA substrate and water.

It is an additional object to provide compositions and methods of storing and using restriction enzymes which are economical, efficient, and reproducible.

The foregoing and other objects and advantages of the present invention will be apparent from the following description. The description (and accompanying drawing) describe the preferred embodiments of the invention. These embodiments do not necessarily represent the full scope of the invention. Reference should therefore be made to the claims for interpreting the full scope of the invention.

DESCRIPTION OF THE PREFERRED EMBODIMENTS

1. In General

A. Suitable Restriction Enzymes

Figure 1:
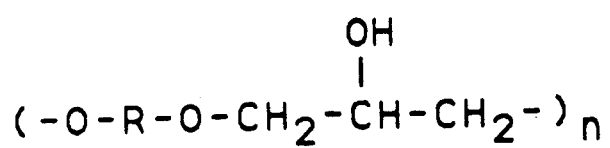
FIG. 1 is a schematic depiction of Ficoll 400, a preferred stabilizer.

The present invention should be suitable for use with all type II restriction endonucleases. Our tests have been conducted on a variety of different restriction endonucleases (Hae III, Pal I, Pst I, Eco RI and Hinf I). These particular enzymes were selected as examples for study because they are commonly used enzymes that are known to exhibit star activity.

B. Stabilizers

By the term "glassified", we mean an under-cooled liquid with a very high viscosity. A glass normally presents an extremely slow diffusive process. The glass transition temperature, "$T_g$," defines the temperature at which a glass changes phase. Upon temperatures higher than the $T_g$, a rubber-like material is formed from the glass. If the temperature continues to increase, the material eventually becomes a fluid. Compounds with a higher $T_g$ will remain at a glass stage at higher temperatures. Residual moisture in the glass will depress a $T_g$ value.

The preferred glassified composition is composed of a suitable stabilizer that is hydrophilic, so that water can readily dissolve the glass and present the restriction enzyme in an aqueous solution. The stabilizer substance should typically display a $T_g$ in a range from 20° to 180° C., preferably 30° C. to 80° C. If the $T_g$ of a glass is well above average room temperature, the glass is better able to withstand storage on a laboratory shelf where the actual temperature may vary somewhat. The $T_g$ of a formulated composition is typically 5° below the $T_g$ of the stabilizer. Preferably, the stabilizer substance will be chemically inert towards the restriction enzyme.

Carbohydrates (e.g. polyhydroxy aldehydes or ketones, such as those with a $(CH_2O)_n$ empirical formula, and their derivatives) are suitable stabilizers. Preferred carbohydrates may be either sugars or polysaccharides. Suitable carbohydrates may be either linear or branched, and may have one or more sugar moieties linked via various linkages. Particularly preferred carbohydrate stabilizers are polysaccharides such as Ficoll, dextran and trehalose. Ficoll is a highly branched polymer that has a molecular weight of 5000 to 1,000,000 and is made by copolymerization of sucrose and epichlorohydrin. A particularly advantageous form of Ficoll is Ficoll 400 which has a molecular weight of 400,000. Ficoll is commercially sold by Pharmacia. FIG. 1 depicts Ficoll. See also U.S. Pat. No. 3,300,474. Other suitable sugars and polysaccharides with appropriate Tg values are maltose, sucrose, cellobiose, maltotriose, polydextrose, mannitol, sorbitol and inulin.

C. Formation of Glassified Restriction Enzymes

The general process of glassification involves first combining an aqueous solution of the restriction enzyme with a supply of the stabilizer. Preferably, the restriction enzyme preparation is free of glycerol (or prepared at a concentration of less than 1% glycerol). The stabilizer is present at a concentration of at least 10% by weight, preferably 30%. When higher concentrations of enzyme are used, it is preferable to use more Ficoll. For example, when more than 100 units Pst I are present per 50 µl of rehydrated reaction mixture, the stabilizer substance is preferably at least 30% (w/w) Ficoll. The level of enzyme giving rise to star activity varies from enzyme to enzyme.

In this regard, a high concentration of certain stabilizers such as Ficoll can surprisingly permit high concentrations of enzymes to be used for cleavage without significant star activity. Note that wholly apart from the effect of glycerol, many restriction enzymes in the prior art exhibited star activity when present in high concentration in a DNA cleavage reaction.

The restriction enzyme is preferably glassified in the presence of a complete reaction buffer, as opposed to a standard storage buffer. Unlike conventional storage buffers which omit $MgCl_2$, a restriction enzyme reaction buffer contains all components necessary to facilitate a restriction enzyme digestion. Such components usually include optimized amount of various salts, such as Tris-HCl, KCl (or NaCl), DTT, EDTA (and sometimes Triton X-100, BSA, and/or beta-mercaptoethanol). In particular $Mg^{+2}$, preferably as $MgCl_2$, should be included in the reaction buffer because restriction enzymes require this ion. It should be noted that Mg+2 had not previously been incorporated into standard storage buffers because of the perceived problems associated with increased protease activity and contaminating bacterial growth in the presence of $MgCl_2$.

The restriction enzyme/buffer formulation is processed into a glass or amorphous state by evaporation of water in a vacuum, preferably at room temperature, followed by additional removal of water at 50° C. The final formulation preferably contains less than 4% water and has a glass transition point of at least 30° C. The resulting formulation should be stable at room temperature for extended periods. For convenience, the restriction enzyme/buffer formulation may be placed into individual tubes in amounts sufficient for a single enzyme digest.

D. Restriction Enzyme Digest

To carry out a restriction digestion using the glassified restriction enzyme, the DNA substrate and water is introduced into a tube containing the glassified composition. The water quickly dissolves the glassified enzyme. Restriction digestions can then be carried out at standard temperature and time of incubation, such as those described in T. Maniatis pages 5.3–5.32, "Restriction And DNA Methylation Enzymes" in *Molecular Cloning* (1989). (This article and all other references are hereby incorporated by reference as if the reference were set out herein.)

2. Example: Hae III

Hae III restriction enzyme may be obtained commercially. One should first dalyze the commercial preparation to remove glycerol. Preferably, Ficoll or another stabilizer is added before dialysis.

As an alternative, we isolated Hae III through standard column chromatography methods. It will be appreciated that other type II restriction enzymes are available and could instead be used. The enzyme was initially stored in the following glycerol-less buffer:

| |
|---|
| 10 mM Tris-HCl (pH 7.5) |
| 50 mM KCl |
| 1 mM DTT |
| 0.1 mM EDTA |
| 20% Ficoll |

The enzyme was then titrated to determine unit concentration. A "Unit" of Hae III is defined for purposes of this patent as the amount of enzyme needed to hydrolyze 1 μg of lambda DNA to completion in 60 minutes at 37° C., in a total assay mixture of 50 μl. One particular batch of enzyme we examined was 50 U/μl. The preferred enzyme concentration is greater, but almost any concentration is suitable for use in the present invention.

In the case of our 50 U/μl Hae III sample, after determining the enzymatic units, the following additions were made to individual 1.5 ml Eppendorf polypropylene tubes:

| Hae III/tube | Hae III (50 U/μl) | BSA (10 mg/ml) | Storage Buffer | Reaction Buffer |
|---|---|---|---|---|
| 100 Units | 2 μl | 0.5 μl | 18 μl | 10 μl |
| 500 Units | 10 μl | 0.5 μl | 10 μl | 10 μl |

Reaction buffer is:
250 mM Tris-HCl (pH 7.6)
250 mM KCl
50 mM $MgCl_2$

The samples were then dried in a vacuum oven at a vacuum of 25 in. Hg, room temperature, overnight (primary drying). The next day, drying was continued at 50° C., 25 in. Hg for 2 hours (secondary drying). The tubes were capped under nitrogen and stored at room temperature in a desiccator.

After storage, we dissolved the glassified composition in 50 μl of filtered, sterile water containing 1 μg of the DNA template. In a particular experiment, the DNA template was φX174 DNA. Any DNA preparation is suitable for the present invention. By "DNA" we mean naturally occurring DNA and synthetic DNA, as well as derivatives thereof, such as methylated or radiolabelled versions.

The reaction tube wa incubated at 37° C. for approximately 12 hours. This digestion time could be shortened by the addition of more enzyme. After digestion was completed, the reaction was halted by adding 10 μl of a known stop reagent (0.05% bromphenol blue, 0.1 M EDTA, and 50% glycerol).

Samples of reaction mixtures were electrophoresed in known fashion into an agarose gel (e.g. a 1.1% agarose in TBE buffer). The electrophoresis was run for two hours at 180 V. The gel contained 0.1 μg/ml ethidium bromide to make the DNA fragments visible under UV light. Examination of the electrophoretic gel disclosed complete digestion of sample DNA by all reconstituted Hae III samples. No star activity was observed in any sample.

3. Examination of Other Restriction Enzymes.

We have also examined the restriction enzymes Pal I, Eco RI, Pst I and Hinf I. The enzymes were removed from storage buffer, and a reaction buffer containing Ficoll was substituted. When tested, all enzymes exhibited complete enzymatic activity and a lack of star activity in the presence of Ficoll. Thus, it appears that Ficoll affirmatively reduces star activity.

4. Comparison of Two Samples

For DNA type analysis (e.g. paternity testing), one compares restriction digests of two different DNA samples. Because of reduced star activity, introducing the results of these digests as evidence in legal proceedings should be facilitated because the digests are more definitive.

Other Variants

It should be appreciated that the invention will work with a wide variety of DNA samples by using the compositions of the present invention in place of the refrigerated prior art compounds. In optimizing the reaction buffers for other restriction enzymes, one may begin by examining the reaction conditions already used, but omitting glycerol. Thus, the invention is intended to be useful for a wide range of DNA and enzymes.

We claim:

1. A glassified composition comprising a glassified carbohydrate stabilizer having dispersed in it a Type II restriction enzyme selected from the group consisting of Type II enzymes that use $Mg^{+2}$ as a co-factor for digesting DNA, and an amount of $Mg^{+2}$, wherein less than 5% of the weight of the composition is glycerol and wherein the amount of $Mg^{+2}$ is sufficient to facilitate restriction enzyme digestion of DNA having a restriction site that the enzyme recognizes upon hydration of the glassified composition while not interfering with stability during long term room temperature storage of the glassified composition wherein the enzyme is selected from the group consisting of HaeIII and HinfI and wherein the amount of $M_g^{+2}$ in the glassified composition provides about 10 mM $Mg^{+2}$ in the digestion solution.

2. The composition of claim 1, wherein the stabilizer is chosen from the group consisting of sugar and polysaccharides.

3. The composition of claim 1, further comprising all reaction reagents other than additional water needed for the composition to cleave a selected DNA having a restriction site that the enzyme is normally capable of cleaving.

4. The composition of claim 1, wherein the stabilizer is at least 30% of the weight of the composition and less than 1% of the weight of the composition is glycerol.

5. The composition of claim 1, wherein the restriction enzyme is Hae III and the composition is suitable to be used for cleavage of DNA upon the addition of water.

6. A method of cleaving DNA comprising adding water and DNA to the composition of claim 1 and then allowing cleavage of the DNA to occur.

7. A method of comparing two DNA samples, comprising separately adding the samples to two different containers, adding the composition of claim 1 and water to each container, allowing cleavage of each sample to occur, and comparing the cleaved samples.

* * * * *